United States Patent [19]

Ezenwa et al.

[11] Patent Number: 5,063,937
[45] Date of Patent: Nov. 12, 1991

[54] MULTIPLE FREQUENCY BIO-IMPEDANCE MEASUREMENT SYSTEM

[75] Inventors: Bertram N. Ezenwa, Centerville; William P. Couch, Fairborn, both of Ohio

[73] Assignee: Wright State University, Dayton, Ohio

[21] Appl. No.: 581,579

[22] Filed: Sep. 12, 1990

[51] Int. Cl.$^5$ ............................................. A61B 5/05
[52] U.S. Cl. ..................................... 128/723; 128/734
[58] Field of Search ..................... 128/734, 723, 693; 331/DIG. 2

[56] References Cited

U.S. PATENT DOCUMENTS

| Re. 30,101 | 9/1979 | Kubicek et al. . | |
|---|---|---|---|
| 3,452,743 | 7/1969 | Rieke | 128/723 |
| 3,566,233 | 2/1971 | Kahn | 128/734 |
| 3,730,171 | 5/1973 | Namon | 128/734 |
| 3,742,936 | 7/1973 | Blanc | 128/693 |
| 3,835,840 | 9/1974 | Mount . | |
| 3,851,641 | 12/1974 | Toole | 128/734 |
| 3,871,359 | 3/1975 | Pacela | 128/693 |
| 3,874,368 | 4/1975 | Asrican | 128/734 |
| 3,882,851 | 5/1975 | Sigworth | 128/693 |
| 3,924,606 | 12/1975 | Silva | 128/734 |
| 3,949,736 | 4/1976 | Vrana et al. . | |
| 3,996,925 | 12/1976 | Djordjevich . | |
| 4,170,225 | 10/1979 | Criglar | 128/733 |
| 4,259,633 | 3/1981 | Rosenaw . | |
| 4,362,105 | 8/1989 | Walbrou | 331/DIG. 2 |
| 4,450,527 | 5/1984 | Sramek | 128/734 |
| 4,450,527 | 5/1984 | Sramek . | |
| 4,562,843 | 1/1986 | Djordjuich et al. . | |
| 4,692,685 | 9/1987 | Blaze . | |
| 4,780,661 | 10/1988 | Bolomey | 128/734 |
| 4,793,362 | 12/1988 | Tidner . | |
| 4,805,621 | 2/1989 | Heinze | 128/734 |
| 4,807,638 | 2/1989 | Sramek . | |
| 4,810,963 | 3/1989 | Blake-Coleman et al. . | |
| 4,823,797 | 4/1989 | Heinze et al. . | |
| 4,836,214 | 6/1989 | Sramek | 128/734 |
| 4,870,341 | 9/1989 | Pikl et al. . | |
| 4,895,163 | 1/1990 | Libke | 128/734 |
| 4,905,705 | 3/1990 | Kizckevich et al. . | |
| 4,919,145 | 4/1990 | Marriott | 128/734 |
| 4,951,682 | 8/1990 | Petre | 128/734 |

FOREIGN PATENT DOCUMENTS 0344770  12/1989  Israel ................................ 128/734

Primary Examiner—Kyle L. Howell
Assistant Examiner—Robert L. Nasser, Jr.
Attorney, Agent, or Firm—Killworth, Gottman, Hagan & Schaeff

[57] ABSTRACT

The multiple frequency impedance measurement system of the present invention permits noninvasive examination of living tissue at any one of a plurality of frequencies. Precise frequency control is provided by a phase locked loop (PLL) circuit which is adjustable among at least a plurality of frequencies by locking the loop to the output signal generated by a voltage controlled oscillator (VCO) divided by a selectable divisor. By selecting the divisor of the output signal of the VCO, the frequency is changed and, due to the use of a PLL circuit, each selected frequency is stably maintained. Electrodes connecting the circuit to tissue to be monitored are driven by a high-Q filter and buffer amplifier which convert the square wave output from a voltage controlled clipper circuit to a sine wave signal. The clipper circuit receives the output signal from the VCO and is part of a feedback loop which maintains a constant examination current for the system. By monitoring the examination current via a precision resistor, a current reference signal is generated and used in the feedback loop to maintain the current at a substantially constant but selectable level. The reference signal is also used to drive a resistance synchronous detector and a reactance synchronous detector to derive resistance and reactance signals, respectively, which are representative of the resistance and reactance of the tissue at the selected measuring frequency. The resistance and reactance signals are displayed via a shared digital display which is switched between the two signals.

19 Claims, 2 Drawing Sheets

MULTIPLE FREQUENCY BIO-IMPEDANCE MEASUREMENT SYSTEM

BACKGROUND OF THE INVENTION

The present invention relates generally to a system for making impedance measurements of body tissue and, more particularly, to such a "bio-impedance" system which can measure the impedance of body tissue over a range of frequencies.

There are a number of commercially available systems which measure the impedance of body tissue by applying a current or voltage signal to the tissue and measuring the resulting voltage or current to determine the impedance of the tissue which is representative, for example, of fluid content within the tissue. As is well known, such systems can be used to measure blood flow, monitor heart functions, monitor fluid build-up within the lungs and perform similar functions for medically related research and patient treatment. All of the known commercially available systems apply a single frequency signal to make the impedance measurements.

There is a need for a bio-impedance measuring system which is capable of making measurements at any frequency within a range of frequencies to permit the study of electrical impedances of intracellular and extracellular fluid composition. Such measurements are essential for determining total body fluid in an intensive care unit, for trauma situations, for dialysis, for physical fitness evaluations (body fat), and similar applications. Problems encountered in developing multiple frequency bio-impedance measurement systems include the difficulty of maintaining low intensity constant drive current through body tissue loads which vary, and the ability to make consistent and accurate determinations of resistive and reactive impedance components at varying loads and different frequencies.

An impedance measuring system utilizing two different frequency signals is disclosed in U.S. Pat. No. 3,851,641. In this system, two different frequency electrical signals are alternately passed through body tissue with the resulting voltage signals being sensed. In-phase coherent detection is performed to remove out-of-phase signal components. The in-phase voltage signals are subtracted from one another to derive a measure of only the internal impedance of the body tissue.

Two different frequency signals are also used in U.S. Pat. No. 4,793,362 wherein change in body fluid is monitored by placing a pair of electrodes at spaced locations on a body, such as a wrist and diametrically opposed ankle, and passing two different high frequency signals through the body via the electrodes. Another pair of electrodes is place in the current path of the first pair of electrodes for measuring body impedance at the two frequencies. A microprocessor utilizes the impedance measurements in an empirical formula to calculate the change in fluid weight of the body.

Thus, while it is known to measure the impedance of body tissue utilizing a single frequency signal applied to the tissue or two frequency signals alternately applied to the tissue, the need for a multiple frequency bio-impedance measuring system which is capable of making impedance measurements at any frequency within a range of frequencies still remains.

SUMMARY OF THE INVENTION

This prior art need is met by the system of the present invention which permits noninvasive examination of living tissue at any one of a plurality of frequencies. Initially, precise frequency control is provided by a phase locked loop (PLL) circuit which is adjustable among at least a plurality of frequencies by locking the loop to the output signal generated by a voltage controlled oscillator (VCO) divided by a selectable divisor. Thus, by selecting the divisor of the output signal of the VCO, the frequency is changed and, due to the use of a PLL circuit, each selected frequency is stably maintained. Electrodes connecting the circuit to tissue to be monitored are driven by a high-Q filter and buffer amplifier which convert the square wave output from a voltage controlled clipper circuit to a sine wave signal. The clipper circuit receives the output signal from the VCO and is part of a feedback loop which maintains a constant examination current for the system. By monitoring the examination current via a precision resistor, a current reference signal is generated and used in the feedback loop to maintain the current at a substantially constant but selectable level. The reference signal is also used to drive a resistance synchronous detector and a reactance synchronous detector to derive resistance and reactance signals, respectively, which are representative of the resistance and reactance of the tissue at the selected measuring frequency. The resistance and reactance signals are displayed individually or via a shared display, preferably a digital display.

In accordance with one aspect of the present invention, a multiple frequency system provides for the noninvasive examination of living tissue by measuring the impedance of the tissue at any one of a plurality of frequencies via electrode means connecting the system to living tissue to be examined. The system comprises signal generator means for generating a stable frequency output signal which can be selectively varied over a range of frequencies. Electrode drive means apply a substantially constant current examination signal derived from the stable frequency output signal to the electrode means. Current control means is connected between the signal generator means and the electrode drive means for regulating the current level of the constant current examination signal. Signal processor means monitors an impedance signal generated in response to the constant current examination signal and generates an impedance signal representative of the impedance of the tissue, the signal processor means being coupled to the current control means to complete a current control feedback loop for maintaining the current level of the constant current examination signal.

To facilitate use of the system of the present invention, display means is provided for displaying the impedance signal to personnel utilizing the system. Preferably, the display means comprises at least one digital display. To extend the versatility of the system, the impedance signal is processed to comprise a resistance component and a reactance component, and the signal generator means comprises frequency selection means for selecting any one of at least a plurality of frequencies within the range of frequencies available to the signal generator means.

In the preferred embodiment of the present invention, the signal generator means comprises a phase locked loop circuit which comprises: a voltage controlled oscillator having an input and an output; a signal generator for generating a fixed frequency reference signal; a phase detector circuit receiving the fixed frequency reference signal from the signal generator, the phase detector circuit having an output connected to the input of the voltage controlled oscillator, and an input; a programmable divider circuit connected between the output of the voltage controlled oscillator and the input of the phase detector circuit; and, frequency selection means for controlling the programmable divider circuit by generating a frequency selection signal which defines the divisor for the programmable divider, the stable frequency output signal being divided by the divisor and passed to the phase detector circuit which controls the voltage controlled oscillator to stabilize the stable frequency signal at a frequency equal to the fixed frequency multiplied by the divisor. In the preferred embodiment of the present invention, the constant current examination signal is passed through a precision resistor connected in series with the electrode means to monitor the examination signal.

The signal processor means comprises first differential amplifier means connected across the precision resistor for generating the current reference signal representative of the magnitude of the constant current examination signal. Current control is performed by voltage controlled clipper means connected between the signal generator means and the electrode drive means. Current control signal generator means generates a desired current level signal which is passed to error amplifier means. Peak detection means receives the current reference signal from the first differential amplifier means and generates a current signal that varies with the peak amplitude of the current reference signal and is also passed to the error amplifier means. The error amplifier means compares the desired current level signal and the current signal to generate a current control signal which is passed to the voltage controlled clipper means to maintain the constant current examination signal at a substantially constant current level corresponding to the desired current level signal. Preferably, the current control signal generator means includes current selection means for selecting the magnitude of the desired current level signal and thereby the magnitude of the constant current examination signal to further expand system capabilities.

While the present invention can be adapted to operate with two electrodes, it is preferably operated with four electrodes such that the electrode means comprise a first drive electrode for receiving the constant current examination signal, a second drive electrode connected to a system ground potential, and a pair of sense electrodes interposed between the first and second drive electrodes with the signal processor means further comprising second differential amplifier means connected across the pair of sense electrodes for generating an impedance signal. The signal processor means further comprises resistance synchronous detector means receiving the current reference signal and the impedance signal for generating a resistance signal representative of the resistance of the living tissue to which the system is connected.

In the preferred embodiment of the present invention, the signal processor means further comprises phase shifter means receiving the current reference signal for generating a 90 degree phase shifted current reference signal and reactance synchronous detector means receiving the 90 degree phase shifted current reference signal and the impedance signal for generating a reactance signal representative of the reactance of the living tissue to which the system is connected. To facilitate use of the system, display means are provided for displaying the resistance signal and the reactance signal. To reduce system expense, the display means may comprise a single digital display and display switch means for selectively connecting the resistance signal and the reactance signal to the single digital display. The output signals from the system may be improved by ripple filter means interposed between the resistance synchronous detector means and the reactance synchronous detector means and the display means. The electrode drive means may advantageously comprise a high Q filter and a buffer amplifier connected in series between the signal generator means and the electrodes.

To ensure accurate readings from the system of the present invention, preferably the system includes overrange means for signalling an operator of the system if impedances outside a usable range are encountered. When overrange impedances are encountered by the system, the resulting readings can be ignored. Preferably, the overrange means is connected to the display means such that the display can be used to indicate the overrange condition.

It is thus and object of the present invention to provide an improved bio-impedance measuring system which permits noninvasive examination of living tissue at any one of a plurality of frequencies; to provide an improved bio-impedance measuring system which permits noninvasive examination of living tissue at any one of a plurality of frequencies wherein the frequency of an examination current signal is controlled via a phase locked loop; to provide an improved bio-impedance measuring system which permits noninvasive examination of living tissue at any one of a plurality of frequencies wherein the current level of an examination current is maintained at a selectable level via a feedback control loop; and, to provide an improved bio-impedance measuring system which permits noninvasive examination of living tissue at any one of a plurality of frequencies wherein the resistance component of the impedance and the reactance component of the impedance are determined by using synchronous detectors.

Other objects and advantages of the invention will be apparent from the following description, the accompanying drawings and the appended claims.

DETAILED DESCRIPTION OF THE INVENTION

Figure 1:
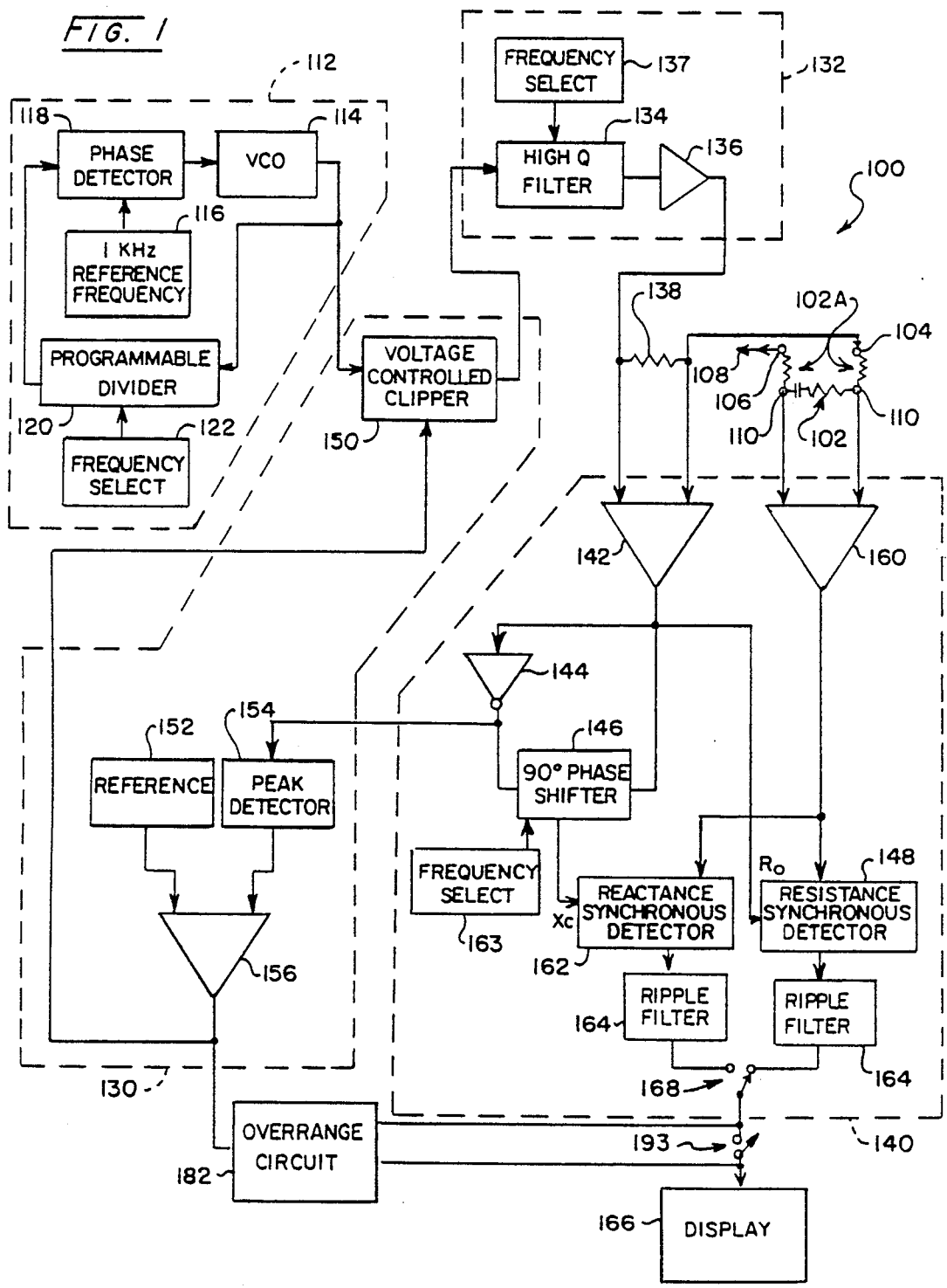
FIG. 1 is a schematic block diagram of a multiple frequency bio-impedance measurement system in accordance with the present invention.

The preferred embodiment of the present invention will now be described with reference to drawing FIG. 1 which illustrates the invention in schematic block diagram form. A multiple frequency bio-impedance system 100 of the present invention provides for noninvasively measuring the impedance of living tissue 102 at any one of a selectable plurality of frequencies. The system 100 is connected to tissue to be measured by electrode means comprising a first drive electrode 104, a second drive electrode 106 which is connected to a system ground 108 and a pair of sense electrodes 110 which are interposed between the first and second drive electrodes 104, 106. Examination current passes through tissue portions 102A in passing through the tissue 102 to be measured. While four electrodes 104, 106, 110 are preferred for the present invention, various aspects of the present invention are also applicable to two electrode impedance measurement systems. A variety of electrodes are commercially available and well known in the art such that their structure and application will not be described in detail in the present application.

The generation of a stable frequency output signal which can be selectively varied over a range of frequencies will now be described with reference to signal generator means comprising a phase locked loop (PLL) circuit 112 in the preferred embodiment. The PLL circuit 112 comprises a voltage controlled oscillator (VCO) 114, a signal generator 116 for generating a fixed frequency reference signal, a phase detector 118, and frequency selection means comprising a programmable divider 120 and a frequency select switch 122. The divisor of the programmable divider 120 is set by the frequency select switch 122 such that the signal received by the divider 120 from the VCO 114 is divided by the currently selected divisor and passed to the phase detector 118.

In the preferred embodiment, the phase detector 118 receives a fixed frequency reference signal of 1 Khz from the signal generator 116 and the output signal from the divider 120. By comparing these two signals, the phase detector 118 generates a DC control voltage for the VCO 114 which control voltage is representative of the difference between the fixed frequency reference signal and the output signal from the divider 120. The DC control voltage for the VCO shifts until the VCO is oscillating at the selected frequency so the PLL circuit 112 is in a stable state.

The output signal from the divider 120 is 1 Khz in frequency if the VCO is oscillating at the selected frequency. Thus, a divisor of 5 results in a 5 Khz output signal from the VCO 114, a divisor of 10 results in a 10 Khz signal, and so forth up to a divisor of 100 for a 100 Khz signal in the preferred embodiment which generates signals within a frequency range of 5 Khz to 100 Khz. Or stated another way, the output signal from the VCO 114 is maintained at a stable frequency which is equal to the fixed frequency generated by the signal generator 116 multiplied by the divisor applied by the divider 120 and set by the frequency select switch 122.

The output signal from the VCO 114 of the signal generator means is passed to current control means 130 which is connected between the signal generator means and electrode drive means 132. The electrode drive means 132 comprises a Hi-Q filter 134 which is used to convert the square wave signal received from the current control means 130 to a sine wave. A buffer amplifier 136 isolates the load including the tissue the impedance of which is to be measured from the filter 134 in order to ensure stable filter operation.

In the preferred embodiment, the filter 134 is a Chebyshev filter with an extremely high peak at the cutoff frequency and a Q equal to 80. A frequency select circuit 137 is controlled to set the center frequency of the filter 134 to correspond to the frequency selected by the frequency select switch 122. The frequency select circuit 137 can be set separately to the desired frequency; however, operation of the system is simplified if the frequency select circuit 137 is gang operated or otherwise slaved to the frequency select switch 122 to ensure that the two are consistent with one another. Thus, the output signal from the buffer amplifier 136 is a sine wave and also the constant current examination signal.

The constant current examination signal is passed through a precision resistor 138 connected in series with the electrodes 104, 110, 106. Signal processor means 140 are connected across the precision resistor 138 and the pair of sense electrodes 110 for monitoring signals generated thereacross. The signal processor means 140 includes first differential amplifier means comprising a wideband differential instrumentation amplifier 142 in the preferred embodiment, connected across the precision resistor 138 for generating a current reference signal. The current reference signal is passed to an inverting amplifier 144, phase shifter means comprising a 90° phase shifter 146 in the preferred embodiment and a resistance synchronous detector 148.

The current control means comprises voltage controlled clipper means 150, current control signal generator means 152 for generating a desired current level signal, peak detection means 154 which also receives the current reference signal after inversion by the inverting amplifier 144, and error amplifier means 156. Current control is performed via a closed feedback loop comprising the voltage controlled clipper means 150, the Hi-Q filter 134, the buffer amplifier 136, the precision resistor 138, the first differential amplifier 142, the inverting amplifier 144, the peak detection means 154 and the error amplifier means 156. Since the precision resistor 138 is in series with the load, the voltage developed across it is proportional to the load current. This voltage is amplified by the amplifier 142, inverted by the amplifier 144 which also serves to buffer and prevent loading of the output signal from the amplifier 144, and converted to a peak DC value by the peak detector 154. The peak voltage from the peak detector 154 is applied to the error amplifier 156, which compares the peak voltage to the desired current level signal generated by the current control signal generator 152.

Any difference between the two is then highly amplified, 80 dB in the preferred embodiment, and used as a control signal for the voltage controlled clipper 150, which varies the amplitude of the constant current examination signal. The loop behaves such that an increase in examination current, which results in an increase of peak detector voltage, results in a decrease of output signal from the error amplifier 156 to the voltage controlled clipper 150, causing a decrease of drive voltage and thereby current. Since the gain of the error amplifier 156 is very high, the system settles to a steady state where the peak detector 154 output is virtually the same as the desired current level signal generated by the current control signal generator 152. Since this can occur only if the current flow through the precision resistor 138 and the load is kept constant, circuit action will maintain the examination current at a constant level substantially corresponding to the desired current level which can be selected via the current control signal generator 152.

The frequency and current selection and stabilization within the multiple frequency bio-impedance system 100 has been described above relative to the phase locked loop (PLL) circuit 112, the current control means 130 and, to a more limited extent, the signal processor means 140. The signal processor means 140 will now be described relative to its primary function of monitoring an impedance signal generated in response to the constant current examination signal and generating an impedance signal representative of the impedance of living tissue being monitored. To this end, the signal processor means 140 further comprises second differential amplifier means, a wideband differential instrumentation amplifier 160 in the preferred embodiment, connected across the pair of sense electrodes 110 for generating an impedance signal.

While the impedance signal could be displayed or utilized directly, in the preferred embodiment it is separated into its resistance and reactance components by the resistance synchronous detector 148 and a reactance synchronous detector 162 which both receive the impedance signal from the amplifier 160. The synchronous detectors 148, 162 comprise multiplier circuits which multiply the impedance signal from the amplifier 160 by an $R_o$ vectored reference for the resistance synchronous detector 160 and by an $X_c$ vectored reference for the reactance synchronous detector 162. The output of the amplifier 142 is used directly as the $R_o$ vectored reference to the resistance synchronous detector 148. The amplifiers 142 and 160 are identically constructed to ensure that the $R_o$ vectored reference signal is at phase 0° with respect to the resistive or $R_o$ component of the impedance represented by the impedance signal from the amplifier 160. Therefore, the resistance synchronous detector 148 does not respond to the reactance component of the impedance signal.

The $X_c$ vectored reference signal is generated by feeding the $R_o$ vectored reference signal from the amplifier 142 into the inverting amplifier 144 to have available a +reference signal and a -reference signal. The +reference signal and the -reference signal are then summed through the 90° phase shifter 146 which comprises an RC network which has its components selected by means of a frequency selection switch 163 such that the summed signal is shifted by 90° with respect to the output signal or +reference signal generated by the amplifier 142. As with the frequency select circuit 137, the frequency select switch 163 can be set separately to the desired frequency; however, operation of the system is simplified if the frequency select switch 163 is gang operated or otherwise slaved to the frequency select switch 122 to ensure that the two or preferably three frequency controls are consistent with one another. The 90° phase shifted signal is then applied to the reactance synchronous detector 162 to extract the reactance component from the impedance signal. Preferably, the 90° phase shifter 146 includes a series of trimpots or potentiometers corresponding to each $X_c$ vectored reference to permit adjustment for each frequency to ensure maximum $R_o$ component rejection by the reactance synchronous detector 162.

The detection of the resistance and reactance components of the impedance signal is based on using precision analog multipliers to multiply the impedance signal or composite signal from the amplifier 160 by the appropriate vectored reference signal to extract the resistance or reactance component. Since the detection is synchronous, the signal which is in phase with the vectored reference signal results in an output signal from the multiplier that is a sine wave having a frequency, 2F, which is twice the frequency of the examination signal which signal touches, but never crosses, zero. The component which is out of phase also results in an output signal having a frequency of 2F, but the wave is precisely centered on zero. Since the load or living tissue being measured will probably consist of both resistance and reactance components, the output signal of the multiplier will consist of signal A, of the desired component, and signal B, of the undesired component summed together. When this composite output signal is filtered or integrated, for example by the ripple filters 164, since the desired component is all positive, it will result in a DC voltage that is proportional to the desired component. And, since the undesired component is centered about zero, its DC valve is zero, and is effectively rejected. The choice of the vectored reference signal determines whether the resistance or the reactance component is treated as the desired component.

The impedance signal, or in the preferred embodiment the resistance and/or reactance signal, is preferably displayed to facilitate use of the multiple frequency bio-impedance system 100 of the present invention. To this end, display means can be provided for displaying the impedance signal, the resistance signal and/or the reactance signal. In the preferred embodiment of the present invention, a single digital display 166 is provided and can be switched between the resistance and reactance signals by switch means comprising an electrical or electronic switch 168.

To ensure stability of the amplifiers 142, 160, preferably a ground plane is used together with RC power supply decoupling at each of the amplifiers 142, 160. Also, ferrite beads are used on the input leads to suppress high frequency oscillations. A symmetrical input scheme may also be used with hand matched resistors to achieve high common mode rejection ratios (CMRR) for the amplifiers 142, 160 It may also be desirable to insert an RC network into one lead of the amplifier 142, with R being identical to the precision resistor 138 and C being adjustable to keep the CMRR of the amplifier 142 high by allowing for compensation of effects caused by the physical layout of the circuit.

Figure 2:
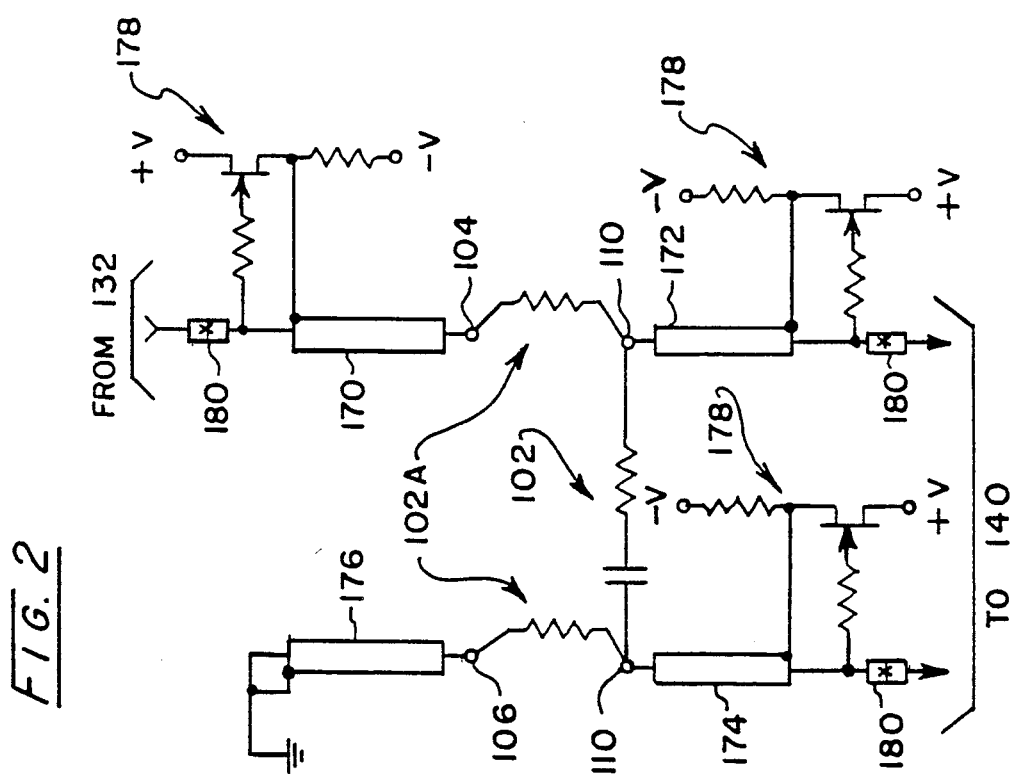
FIG. 2 is a schematic view of a preferred arrangement for coupling the system of the present invention to body tissue for measuring its impedance.

Shielded cables are normally used to connect the system 100 to the living tissue 102 the impedance of which is to be measured. Normally, the shields of the cables are connected to system ground potential. Unfortunately, the capacitance between the center conductor and the shield of a cable appears in parallel with the impedance of the tissue 102 and thus can result in inaccurate readings, particularly at high frequencies. To overcome this problem in the system of the present invention, it is preferred to drive three of the shielded cables 170, 172, 174 by follower amplifiers 178 with the input signals to the amplifiers 178 being the same as the signals which drives the center conductors of the corresponding cables, see FIG. 2. The amplifiers 178 include field effect transistors FET's (MPF 102) connected as follower amplifiers having a gain of 0.92. The coupling arrangement shown in FIG. 2 reduces the effective capacitance of the shielded cables 170, 172, 174 from approximately 100 pf to approximately 8 pf without affecting the shielding of the cables 170, 172, 174 since the buffer amplifier 136 has a very low output impedance. The ferrite beads previously referred to are shown in FIG. 2 and indicated by the numeral 180.

Figure 3:
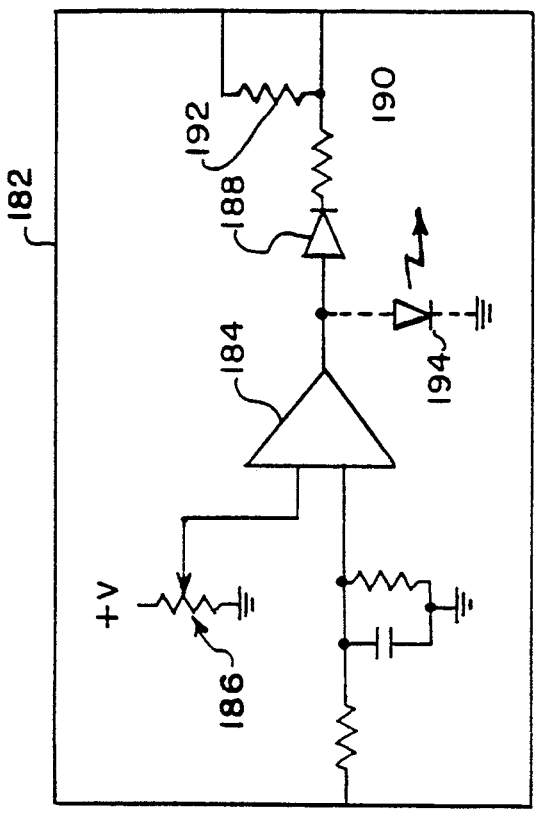
FIG. 3 is a schematic diagram of an overrange circuit which can be used in the present invention.

To help ensure that the present system is operated in a manner which always indicates accurate readings, an overrange circuit 182 is shown in FIGS. 1 and 3. In the preferred embodiment, the overrange circuit 182 is connected between the error amplifier 156 of the current control means 130 and the input to the digital display 166. The signal from the error amplifier 156 is continuously monitored and converted to a DC signal which is connected to a comparator circuit 184 which can be adjusted via a potentiometer 186.

If the DC signal is above a value proportional to the maximum impedance which can be accurately monitored by the system of the present invention, approximately 1400 ohms in one working embodiment, the comparator 184 detects the overrange and forces the input to the digital display 166 to an overrange condition via a diode 188 and resistors 190, 192. Dependent upon the particular display which is used, overrange is indicated by flashing the maximum number which can be displayed or in some other way preventing reading and immediately indicating the overrange condition such that it cannot be overlooked. The overrange circuit 182 can be overridden by operation of a switch 193.

An alternate overrange indication could be provided by means of a light emitting diode (LED) 194 or other device which would signal the user of the system. It is believed that such overrange indications are less desirable than overranging the display 166 since an operator could possibly not notice the overrange signal.

Having thus described the multiple frequency bioimpedance measurement system of the present invention in detail and by reference to preferred embodiments thereof, it will be apparent that modifications and variations are possible without departing from the scope of the invention defined in the appended claims.

What is claimed is:

1. A multiple frequency system for the noninvasive examination of living tissue by measuring the impedance of the tissue at any one of a plurality of frequencies, said system being adapted to be connected to the living tissue to be examined by electrode means and comprising:
    signal generator means for generating a stable frequency output signal which can be selectively varied over a range of frequencies;
    electrode drive means for applying a substantially constant current examination signal derived from said stable frequency output signal to said electrode means;
    current control means connected between said signal generator means and said electrode drive means for regulating the current level of said constant current examination signal; and
    signal processor means for monitoring an impedance signal generated in response to said constant current examination signal and generating an impedance signal representative of the impedance of said tissue, said signal processor means being coupled to said current control means to complete a current control feedback loop for maintaining the current level of said constant current examination signal.

2. A multiple frequency system for the noninvasive examination of living tissue by measuring the impedance of the tissue at any one of a plurality of frequencies as claimed in claim 1 further comprising display means for displaying said impedance signal.

3. A multiple frequency system for the noninvasive examination of living tissue by measuring the impedance of the tissue at any one of a plurality of frequencies as claimed in claim 2 wherein said display means comprises at least one digital display.

4. A multiple frequency system for the noninvasive examination of living tissue by measuring the impedance of the tissue at any one of a plurality of frequencies as claimed in claim 1 wherein said signal processor means comprises means for generating said impedance signal as a resistance component and a reactance component.

5. A multiple frequency system for the noninvasive examination of living tissue by measuring the impedance of the tissue at any one of a plurality of frequencies as claimed in claim 1 wherein said signal generator means comprises frequency selection means for selecting at least a plurality of frequencies within said range of frequencies.

6. A multiple frequency system for the noninvasive examination of living tissue by measuring the impedance of the tissue at any one of a plurality of frequencies as claimed in claim 1 wherein said signal generator means comprises a phase locked loop circuit.

7. A multiple frequency system for the noninvasive examination of living tissue by measuring the impedance of the tissue at any one of a plurality of frequencies as claimed in claim 6 wherein said phase locked loop circuit comprises:
    a voltage controlled oscillator having an input and an output;
    a signal generator for generating a fixed frequency reference signal;
    a phase detector circuit receiving the fixed frequency reference signal from said signal generator, said phase detector circuit having an output connected to the input of said voltage controlled oscillator, and an input;
    a programmable divider circuit connected between the output of said voltage controlled oscillator and the input of said phase detector circuit; and
    frequency selection means for controlling said programmable divider circuit by generating a frequency selection signal which defines the divisor for said programmable divider, said stable frequency output signal being divided by said divisor and passed to said phase detector circuit which controls said voltage controlled oscillator to stabilize said stable frequency signal at a frequency equal to said fixed frequency multiplied by said divisor.

8. A multiple frequency system for the noninvasive examination of living tissue by measuring the impedance of the tissue at any one of a plurality of frequencies as claimed in claim 1 wherein said constant current examination signal is passed through a precision resistor connected in series with said electrode means, said signal processor means comprises first differential amplifier means connected across said precision resistor for generating a current reference signal, and said current control means comprises:
    voltage controlled clipper means connected between said signal generator means and said electrode drive means;
    current control signal generator means for generating a desired current level signal;
    peak detection means receiving said current reference signal from said first differential amplifier means and generating a current signal that varies with the peak amplitude of said current reference signal; and
    error amplifier means connected to said current control signal generator means and said peak detection means for comparing said desired current level signal and said current signal to generate a current control signal which is passed to said voltage controlled clipper means to maintain said constant current examination signal at a substantially constant level corresponding to said current reference signal.

9. A multiple frequency system for the noninvasive examination of living tissue by measuring the impedance of the tissue at any one of a plurality of frequencies as claimed in claim 8 wherein said current control signal generator means includes current selection means for selecting the magnitude of said desired current level signal and thereby the magnitude of said constant current examination signal.

10. A multiple frequency system for the noninvasive examination of living tissue by measuring the impedance of the tissue at any one of a plurality of frequencies as claimed in claim 8 wherein said electrode means comprise a first drive electrode for receiving said constant current examination signal, a second drive electrode connected to a system ground potential and a pair of sense electrodes interposed between said first and second drive electrodes, said signal processor means further comprising second differential amplifier means connected across said pair of sense electrodes for generating an impedance signal.

11. A multiple frequency system for the noninvasive examination of living tissue by measuring the impedance of the tissue at any one of a plurality of frequencies as claimed in claim 10 wherein said signal processor means further comprises resistance synchronous detector means receiving said current reference signal and said impedance signal for generating a resistance signal representative of the resistance of the living tissue to which the system is connected.

12. A multiple frequency system for the noninvasive examination of living tissue by measuring the impedance of the tissue at any one of a plurality of frequencies as claimed in claim 11 wherein said signal processor means further comprises:
  phase shifter means receiving said current reference signal for generating a 90 degree phase shifted current reference signal; and
  reactance synchronous detector means receiving said 90 degree phase shifted current reference signal and said impedance signal for generating a reactance signal representative of the reactance of the living tissue to which the system is connected.

13. A multiple frequency system for the noninvasive examination of living tissue by measuring the impedance of the tissue at any one of a plurality of frequencies as claimed in claim 12 further comprising ripple filter means interposed between said resistance synchronous detector means and said reactance synchronous detector means.

14. A multiple frequency system for the noninvasive examination of living tissue by measuring the impedance of the tissue at any one of a plurality of frequencies as claimed in claim 12 further comprising display means for displaying said resistance signal and said reactance signal.

15. A multiple frequency system for the noninvasive examination of living tissue by measuring the impedance of the tissue at any one of a plurality of frequencies as claimed in claim 14 wherein said display means comprises a single digital display and display switch means for selectively connecting said resistance signal and said reactance signal to said single digital display.

16. A multiple frequency system for the noninvasive examination of living tissue by measuring the impedance of the tissue at any one of a plurality of frequencies as claimed in claim 1 wherein said electrode drive means comprises a high Q filter and a buffer amplifier connected in series between signal generator means and said electrodes.

17. A multiple frequency system for the noninvasive examination of living tissue by measuring the impedance of the tissue at any one of a plurality of frequencies as claimed in claim 1 further comprising overrange indicator means for signalling an operator of the system if impedances outside a usable range are encountered.

18. A multiple frequency system for the noninvasive examination of living tissue by measuring the impedance of the tissue at any one of a plurality of frequencies as claimed in claim 17 wherein said overrange indicator means is connected to said current control means.

19. A multiple frequency system for the noninvasive examination of living tissue by measuring the impedance of the tissue at any one of a plurality of frequencies as claimed in claim 18 further comprising display means for displaying said impedance signal, said overrange indicator means also being connected to said display means.

* * * * *